(12) United States Patent
Qin et al.

(10) Patent No.: US 6,858,732 B2
(45) Date of Patent: Feb. 22, 2005

(54) PHOTOCHROMIC BENZODIOXINE FUSED NAPHTHOPYRAN COMPOUNDS, COMPOSITIONS AND ARTICLES CONTAINING THOSE NAPHTHOPYRAN COMPOUNDS

(75) Inventors: Xuzhi Qin, Hacienda Heights, CA (US); J. Thomas Ippoliti, St. Paul, MN (US)

(73) Assignee: Vision-Ease Lens, Inc., Ramsey, MN (US)

(*) Notice: Subject to any disclaimer, the term of this patent is extended or adjusted under 35 U.S.C. 154(b) by 29 days.

(21) Appl. No.: 10/090,594

(22) Filed: Mar. 1, 2002

(65) Prior Publication Data

US 2003/0168645 A1 Sep. 11, 2003

(51) Int. Cl.[7] ............... C07D 405/00; C07D 409/00; C07D 313/00; C07D 309/00; C07D 335/04
(52) U.S. Cl. ............... 546/41; 546/280.1; 546/282.4; 546/282.7; 549/12; 549/24; 549/25; 549/41; 549/354; 549/358
(58) Field of Search ............... 546/41, 280.1, 546/282.4, 282.7; 549/12, 24, 25, 41, 354, 358

(56) References Cited

U.S. PATENT DOCUMENTS

| | | | |
|---|---|---|---|
| 3,567,605 A | 3/1971 | Becker | 204/158 |
| 3,627,690 A | 12/1971 | Casella et al. | 252/300 |
| 4,826,977 A | 5/1989 | Heller et al. | 544/70 |
| 5,200,116 A | 4/1993 | Heller | 252/586 |
| 5,238,981 A | 8/1993 | Knowles | 524/110 |
| 5,411,679 A | 5/1995 | Kumar | 252/586 |
| 5,429,744 A | 7/1995 | Hagqvist | 210/493.1 |
| 5,451,344 A | 9/1995 | Knowles et al. | 252/586 |
| 5,458,814 A | 10/1995 | Kumar et al. | 252/586 |
| 5,645,767 A | 7/1997 | Van Gemert | 252/586 |
| 5,651,923 A | 7/1997 | Kumar et al. | 252/586 |
| 5,698,141 A | 12/1997 | Kumar | 252/586 |
| 6,018,059 A | 1/2000 | Chan | 549/382 |
| 6,348,604 B1 | 2/2002 | Nelson et al. | 549/389 |

FOREIGN PATENT DOCUMENTS

| | | | |
|---|---|---|---|
| WO | WO 95/05382 | 2/1995 | C07D/491/04 |
| WO | WO 96/14596 | 5/1996 | G02B/5/23 |
| WO | WO 97/21698 | 6/1997 | C07D/311/78 |

*Primary Examiner*—Rita Desai
*Assistant Examiner*—Raymond Covington
(74) *Attorney, Agent, or Firm*—Mark A. Litman & Assoc. P.A.

(57) ABSTRACT

Benzodioxino-naphtho[1,2-b]pyran compounds having particularly advantageous photochromic properties, such as, high sensitivity/coloration, two distinct absorption bands in the 430–500 nm range and 520–620 nm range of the visible spectrum may be generally described as a naphthopyran having a central nucleus of the formula:

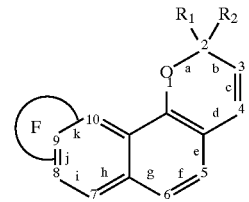

wherein F is a 1,4-benzodioxine ring

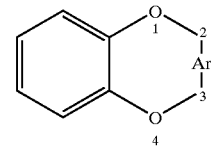

with its 2,3 positions fused to the i, j, or k faces; and $R_1$ and $R_2$ are the atoms or groups providing photochromic properties to the naphthopyran.

21 Claims, No Drawings

PHOTOCHROMIC BENZODIOXINE FUSED NAPHTHOPYRAN COMPOUNDS, COMPOSITIONS AND ARTICLES CONTAINING THOSE NAPHTHOPYRAN COMPOUNDS

BACKGROUND OF THE INVENTION

1. Field of the Invention

The present invention relates to novel naphthopyran-type compounds that have, in particular, photochromic properties. The invention also relates to photochromic compositions and photochromic ophthalmic articles (goggles, lenses and eye-shields, for example) that contain these naphthopyrans. The invention also covers the preparation of these novel naphthopyrans. The photochromic compounds are capable of changing color under the influence of a first poly-chromatic or mono-chromatic range of luminous radiation (UV radiation for example) and of returning to their initial color when the luminous irradiation ceases, or under the influence of temperature and/or poly- or mono-chromatic light different from the first light. The invention particularly relates to naphthopyrans having a benzodioxine group fused to the naphthalene core.

2. Background of the Art

Photochromism generally concerns the ability of a compound to reversibly change color under different light conditions. One particular type of photochromic phenomenon concerns the reversible change in color of a compound from an original color to a different color when the compound is exposed to a source of ultraviolet radiation, such as solar radiation or light radiated from a mercury or xenon lamp. The photochromic compound fades to the original color within a period of time after the photochromic compound is isolated from the ultraviolet radiation This can be done, for example, by placing the compound in a dark room.

Photochromic compounds find applications in various fields, such as for the manufacture of ophthalmic lenses, contact lenses, solar protection glasses, goggles, sun screens, filters, camera optics, photographic apparatus optics or other optical devices and observation devices, glazing, decorative objects, currency elements and even for information storage by optical inscription (coding). For example, photochromic compounds, such as naphthopyrans, are incorporated into plastic ophthalmic lenses to effect color changes in the lenses when the lenses are exposed to particular lighting conditions. Additionally, different photochromic compounds may be blended together to create a color effect that is different from respective color effects of the individual photochromic compounds. As an example, a first photochromic compound that turns orange or red when activated by light and a second photochromic compound that turns blue when activated by light may be blended together to form a photochromic mixture that produces a shade of gray when activated by light.

In the field of ophthalmic optics, and in particular the field of spectacles, a photochromic lens that comprises one or more photochromic compounds is usually required to have:

- a high transmission level in the visible region in the absence of ultraviolet radiation,
- a low transmission (high colorability) under solar irradiation (especially with ultraviolet radiation exposure),
- desired coloration and discoloration kinetics, e.g., high sensitivity to irradiation and fast bleaching,
- a high solubility in hosting materials,
- a tint acceptable to the consumer (gray or brown preferably) with the chosen tint maintained during the coloration and the discoloration of the lens,
- a maintenance of the performance and properties, within a temperature range of 0–40° C.,
- a significant durability, since these objectives sought after are used in sophisticated corrective lenses and are therefore expensive.

These lens characteristics are primarily determined by the active photochromic compounds. These compounds must furthermore be compatible with the organic or inorganic support that constitutes the lens.

Moreover, it is to be noted that obtaining a neutral, gray or brown tint may necessitate the use of at least two photochromes of different colors, i.e., two separate compounds having distinct maximal absorption wavelengths in the visible region of the electromagnetic spectrum. The use of combinations of photochromic compounds imposes other requirements on both the individual photochromic compounds and the groups of photochromic compounds combined. In particular, the coloration and discoloration kinetics of the (two or more) combined active photochromic compounds must be essentially identical. The same applies for their stability with time, and also for their compatibility with a single plastic or inorganic support.

Amongst the numerous photochromic compounds described in the prior art, benzopyrans or naphthopyrans are described in patents or patent applications U.S. Pat. Nos. 3,567,605; 3,627,690; 4,826,977; 5,200,116; 5,238,981; 5,411,679; 5,429,744; 5,451,344; 5,458,814; 5,651,923; 5,645,767; 5,698,141; 6,018,059; 6,296,785; WO-A-95 05382; WO-A-96-14596; WO-A-97 21698 which are of the reduced formulae below:

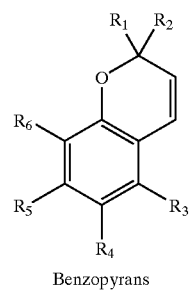 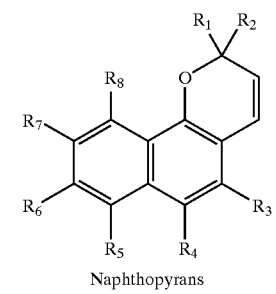

Benzopyrans       Naphthopyrans

U.S. Pat. Nos. 5,651,923 and 6,018,059 more specifically describe naphthopyrans having benzofurano or naphthofurano groups fused to the naphthalene ring of naphthopyran (the general structures are shown below).

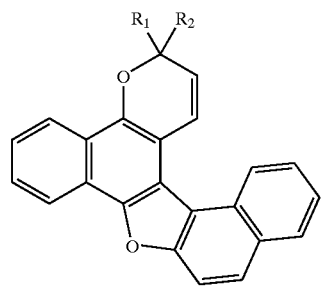

U.S. Pat. No. 5,651,923

-continued

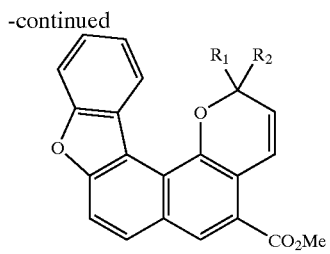

U.S. Pat. No. 5,651,923

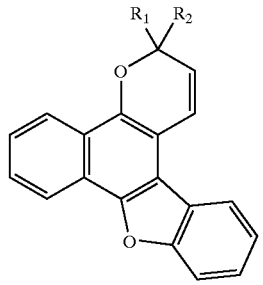

U.S. Pat. No. 6,018,059

The various substitutent groups are defined in the various patents and encompass a wide, art-accepted range of combinations of substitutents intended to provide specific physical or photochromic properties. These compounds claim to satisfy the specifications identified above as needed for photochromic compounds. In reality, even if these compounds really do have one or more of the basic properties sought after, such as a high transmission in the absence of ultraviolets and a high colorability under solar irradiation, none of the compounds described hitherto have the complete combination of properties necessary for the production of satisfactory articles. In particular, none of these compounds is intrinsically gray or brown, and the necessity of using an additional photochromes in order to obtain one of these two tints does persist.

In this context, it is to the credit of the applicants to have been interested in this type of derivatives as a base for developing novel photochromes, and for having found, in a surprising way, that benzodioxine fused naphthopyrans possess particularly advantageous photochromic properties. More precisely, these compounds exhibit higher sensitivity to solar radiation and higher $\lambda_{max}$ values than the naphthopyran analogues, and possess, for certain derivatives, two intense absorption bands in the visible spectrum region. This type of photochromic molecules, which is novel per se, adapts well in association with other complementary photochromic dyes in order to give ray or brown tints.

SUMMARY OF THE INVENTION

The present invention discloses novel benzodioxino-naphtho[1,2-b]pyran compounds having particularly advantageous photochromic properties, such as, high sensitivity/coloration, two absorption bands in the 430–500 nm range and 520–620 nm range of the visible spectrum.

According to a first aspect of the invention is described a naphthopyran having a central nucleus of the formula:

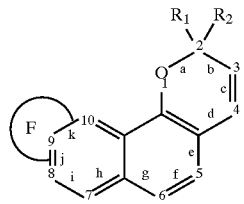

wherein F is a 1,4-benzodioxine ring with its 2,3 positions fused to the i, j, or k faces;

$R_1$ and $R_2$ are the atoms or groups providing photochromic properties to the naphthopyran, such atoms, for example, being narrowly represented by hydrogen and halogen atoms, and such groups being narrowly represented by organic groups, as further described below.

This naphthopyran may preferably have $R_1$ is selected from the group consisting of a hydrogen, a linear or branched alkyl group of 1 to 12 carbon atoms, a cycloalkyl group of 3 to 12 carbon atoms, an aryl group of 6 to 24 ring carbon atoms or a heteroaryl group of 4 to 24 carbon atoms and at least one hetero ring atom selected from sulfur, oxygen and nitrogen; and wherein $R_1$ and $R_2$ together form a heterocyclic ring, such as an adamantyl, norbomyl, fluorenylidene, di($C_1$–$C_6$)alkylanthracenylidene or spiro($C_5$–$C_6$) cycloalkylanthracenylidene group. The organic groups may be attached to this position through a carbon atom or through a heteroatom (e.g., N, O, S, etc.), or a linking group.

Another aspect of the invention is a naphthopyran having the central nucleus of the formula:

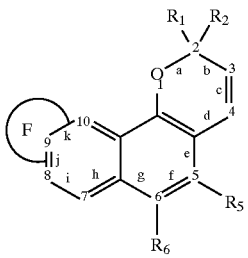

wherein F is a 1,4-benzodioxine ring with its 2,3 positions fused to the i, j, or k faces;

$R_1$ and $R_2$ are the atoms or groups necessary to provide photochromic properties to the naphthopyran (as described above), and $R_5$ and $R_6$ are selected from the group consisting of:
a hydrogen,
a halogen,
a linear or branched alkyl group of 1 to 12 carbon atoms,
a cycloalkyl group of 3 to 12 carbon atoms,
a linear or branched alkoxy group of 1 to 12 carbon atoms,
a linear or branched alkenyl or alkynyl group of 1–12 carbon atoms,
a linear or branched alkenyloxy or alkynyloxy group of 1–12 carbon atoms,
an aryl or heteroaryl group, and
an aralkyl or heteroaralkyl group, the alkyl group, which is linear or branched, of 1 to 4 carbon atoms.

According to another aspect of the present invention, naphthopyran compounds of the following formula (I) are described and enabled:

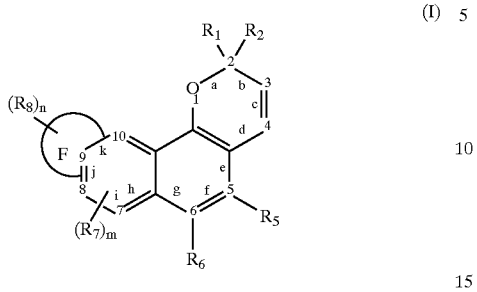

in which:

F is a 1,4-benzodioxine ring with its 2,3 positions fused to the i, j, or k side of the naphthopyran as identified in Formula (I);

$R_1$ and $R_2$, for example, may independently represent:
- a hydrogen,
- a linear or branched alkyl group which comprises 1 to 12 carbon atoms (with or without substitution),
- a cycloalkyl group which comprises 3 to 12 carbon atoms,
- an aryl or heteroaryl group which comprises in its basic structure (that is, in its ring atoms, the rings comprising 5, 6 or 7 atoms) 6 to 24 carbon atoms or 4 to 24 carbon atoms respectively and at least one heteroatom selected from sulfur, oxygen and nitrogen; the basic structure being optionally substituted with at least one substituent selected from:
  - a halogen atom (e.g., fluorine, chlorine and bromine),
  - a hydroxy group,
  - a linear or branched alkyl group comprising 1 to 12 carbon atoms,
  - a linear or branched alkoxy group comprising 1 to 12 carbon atoms,
  - a haloalkyl or haloalkoxy group corresponding to the ($C_1$–$C_{12}$) alkyl or alkoxy groups above respectively which are substituted with at least one halogen atom, and notably a fluoroalkyl group of this type,
  - a linear or branched alkenyl group comprising 2 to 12 carbon atoms, and notably a vinyl group or an allyl group,
  - an amino group:

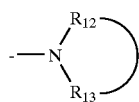

in which $R_{12}$ and $R_{13}$, which are the same or different, independently representing a hydrogen, a linear, branched, or cyclic alkyl group comprising 1 to 6 carbon atoms, an aryl or heteroaryl group, or representing (together with the nitrogen atom to which they are bound) a 5- to 7-membered ring which can comprise at least one other heteroatom selected from oxygen, sulfur and nitrogen, said nitrogen being optionally substituted with an $R_{10}$ group, which is a linear or branched alkyl group comprising 1 to 6 carbon atoms, a phenyl, a benzyl, or a naphthyl,
- a methacryloyl group or an acryloyl group,
- an aralkyl or heteroaralkyl group, the alkyl part of which is linear or branched, comprising 1 to 4 carbon atoms and the aryl and heteroaryl groups having the definitions given above, or
- the two substituents $R^1$ and $R^2$ together forming ring group such as those represented by an adamantyl, norbornyl, fluorenylidene, 5,5- or 10,10-di($C_1$–$C_6$) alkylanthracenylidene, 5 (or 10)-($C_1$–$C_6$)alkyl-5 (or 10)-OH (or $OR_{10}$)anthracenylidene or spiro($C_5$–$C_6$) cycloalkylanthracenylidene ring group; said ring group being optionally substituted with at least one of the substituents listed above in the definitions for $R_1$, $R_2$; said ring group being optionally substituted with two adjacent groups that form a 5- to 6-member aromatic or non-aromatic ring which can comprise at least one heteroatom selected from oxygen, sulfur, and nitrogen, or
- either $R_1$ or $R_2$ is mono- or di-substituted phenyl which is substituted in the position para- to the connection side with -phenyl, —($CH2$)$_p$-phenyl or —O—($CH2$)$_p$-phenyl substituted, wherein p is an integer from 1 to 6, and the ring of the substituent group forms part of a second photochromic pyran;

$R_5$ and $R_6$ are identical or different and they represent, independently,
- a hydrogen atom,
- a hydroxy group,
- a halogen atom (e.g., fluorine, chlorine and bromine),
- a linear or branched alkyl group which comprises 1 to 12 carbon atoms (advantageously 1 to 6 carbon atoms),
- a cycloalkyl group comprising 3 to 12 carbon atoms,
- a linear or branched alkoxy group comprising 1 to 12 carbon atoms (most advantageously 1 to 6 carbon atoms),
- a haloalkyl, halocycloalkyl, or haloalkoxy group corresponding to the alkyl, cycloalkyl, alkoxy groups above respectively, which are substituted with at least one halogen atom, notably selected from fluorine, chlorine and bromine,
- a linear or branched alkenyl or alkynyl group comprising 1–12 carbon atoms, preferably a vinyl or allyl group,
- a linear or branched alkenyloxy or alkynyloxy group comprising 1–12 carbon atoms, preferably an allyloxy group,
- an optionally substituted aryl or heteroaryl group selected from phenyl, naphthyl, phenanthryl, pyrenyl, quinolyl, isoquinolyl, benzofuranyl, thienyl, benzothienyl, dibenzofuranyl, dibenzothienyl, carbazolyl, indolyl, said substituents having the same definition as that given above for aryl or heteroaryl groups within the definitions of $R_1$, $R_2$,
- a mono-substituted phenyl having a substituent at the para-position that is a linking group, —($CH_2$)$_t$— or —O—($CH_2$)$_t$—, wherein t is the integer 1, 2, 3, 4, 5 or 6, connected to an aryl group, e.g. phenyl or naphthyl, which is a member of another photochromic naphthopyran, such as naphtho[2,1-b]pyran or naphtho[1,2-b]pyran,
- an aralkyl or heteroaralkyl group, the alkyl part of which is linear or branched, comprising 1 to 4 carbon atoms and the aryl and heteroaryl groups having the definitions given supra,
- a —C($R_{14}$)$_2$X group, wherein X is —CN, halogen, hydroxy, alkoxy, benzoyloxy, $C_1$–$C_6$ acyloxy, amino, $C_1$–$C_6$ mono-alkylamino, $C_1$–$C_6$ dialkyl amino, morpholino, piperidino, 1-indolinyl, pyrrolidyl, or trimethylsilyloxy, $R_{14}$ is hydrogen, $C_1$–$C_6$ alkyl, phenyl or naphthyl with $C_1$–$C_6$ alkyl or $C_1$–$C_6$ alkoxy substituents, an amine or amide group:

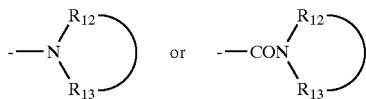

in which $R_{12}$ and $R_{13}$ are defined as in $R_1$ and $R_2$, an —OC(O)$R_{15}$ or —COO$R_{15}$ group, $R_{15}$ representing a straight or branched alkyl group comprising 1 to 6 carbon atoms, or a cycloalkyl group comprising 3 to 6 carbon atoms, or a phenyl group, optionally

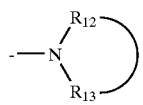

substituted with at least one of the substituents listed above for aryl groups within the definitions of $R_1$, $R_2$, a group —O$R_{16}$, wherein $R_{16}$ is a $C_1$–$C_6$ acyl, an aralkyl or heteroaralkyl group with a $C_1$–$C_3$ alkyl portion and an aromatic portion defined supra in $R_1$ and $R_2$, a ($C_3$–$C_7$)cycloalkyl group, a ($C_2$–$C_4$)alkyl group optionally substituted with $C_1$–$C_6$ alkoxy, fluoro, chloro, or $R_{16}$ is the group, —CH($R_{17}$)$R_{18}$, wherein $R_{17}$ is hydrogen or $C_1$–$C_3$ alkyl and $R_{18}$ is —CN, —CF$_3$, or —COO$R_{19}$, wherein $R_{19}$ is hydrogen or linear, branched, or cyclic alkyl, aralkyl or heteroaralkyl, said aryl substituted with alkyl or alkoxy, a polyether, polyamide, polycarbonate, polycarbamate, polyurea, polyester residue, or a group ended by a polymerizable residue.

Alternatively, $R_5$ and $R_6$ may together form a 5- to 7-member optionally substituted carbocyclic or heterocyclic ring which can comprise at least one heteroatom selected from oxygen, sulfur, and nitrogen, and/or at least one substituent selected from the group consisting of a $C_1$ to $C_6$ alkyl group which is linear or branched, a $C_1$ to $C_6$ alkoxy group which is linear or branched, and an amine group of formula

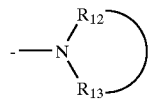

as defined in $R_1$ and $R_2$ for amine groups. The ring may be annelated with one aromatic group. Examples of the carbocyclic ring substituents include cyclopentane, cyclohexane, bicyclo[2,2,1]heptane, etc. Examples of the heterocyclic group include dihyrofuran, dihydropyran, etc. Examples of the aromatic annelated carbocyclic ring include indeno, dihydronaphthaleno, etc. Examples of the aromatic annelated heterocyclic ring include benzofurano, benzodioxino, etc.

In the definitions of $R_5$ and $R_6$, like substituents have like meanings.

$R_7$ and $R_8$ may independently represent:
a hydrogen,
a halogen, and notably fluorine, chlorine or bromine,
a linear or branched alkyl group which comprises 1 to 12 carbon atoms (advantageously 1 to 6 carbon atoms),
a cycloalkyl group comprising 3 to 12 carbon atoms,
a linear or branched alkoxy group comprising 1 to 12 carbon atoms (most advantageously 1 to 6 carbon atoms),
a haloalkyl, halocycloalkyl, or haloalkoxy group corresponding to the alkyl, cycloalkyl, alkoxy groups above respectively, which are substituted with at least one halogen atom, notably selected from fluorine, chlorine and bromine,
a linear or branched alkenyl or alkynyl group comprising 1–12 carbon atoms, preferably a vinyl or allyl group,
a linear or branched alkenoxy or alkynoxy group comprising 1–12 carbon atoms, preferably an allyloxy group,
an aryl or heteroaryl group having the same definition as that given above for aryl or heteroaryl groups within the definitions of $R_1$, $R_2$,
an aralkyl or heteroaralkyl group, the alkyl group, which is linear or branched, comprising 1 to 4 carbon atoms, and the aryl and heteroaryl groups having the same definitions as those given above for $R_1$, $R_2$,
an amine or amide group:

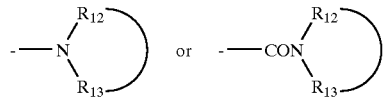

$R_{12}$, and $R_{13}$ having their respective definitions given above for the amine substituents of the values $R_1$, $R_2$, a —C($R_{14}$)$_2R_{15}$, —OCO$R_{15}$, or —COO$R_{15}$ group, wherein $R_{14}$ and $R_{15}$ are defined supra in $R_5$ and $R_6$, a methacryloyl group or an acryloyl group, an epoxy group having the formula,

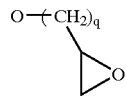

in which q=1, 2 or 3,
a polyether, polyamide, polycarbonate, polycarbamate, polyurea or polyester residue, or a group with polymerizable residue,
n is an integer from 0 to 4, and m is an integer from 0 to 2;

The terms "group" and "central nucleus" have established meanings according to the practice of the present invention. Where the term "group" is used, the chemical unit described is intended to include and allow for substituents consistent with the primary chemical unit. For example, where the term alkyl group is used, that term is intended to include classic alkyl materials such as methyl, ethyl, propyl, butyl, hexyl, octyl, iso-octyl, dodecyl, cyclohexyl and the like, and is also intended to include alkyl units with substitution thereon consistent with the underlying nature of an alkyl unit, such as hydroxymethyl, bromoethyl, dichloropropyl, 1,2,3,4-tetrachlorobutyl, omega-cyanohexyl and the like. Where the term "alkyl moiety" is used, no substitution is allowed.

The terminology of a central nucleus of a provided formula has a similar meaning. The term indicates that the formula, even though atoms are shown in the formula, may be substituted with any chemical units as long as the underlying bond structure of the formula is not altered. For example, where the term a central nucleus of the formula

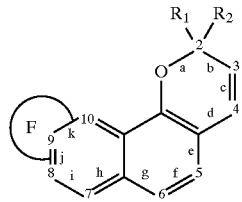

is used, there may be any substitution at such positions as 2, 3, 4, 5, 6, 7, 8, 9, or 10 as long as the structure of F is not destroyed and the bond structure shown (e.g., the double bonds) are not converted to single bonds (e.g., by attempting to provide two substituents at the 6-position, which would require elimination of the double bond between positions 5 and 6. Where the term a compound of the formula is used, except for description of the term 'group' in definitions, no unspecified substitution is allowed.

Where the term 'group' or 'central nucleus' is used in the practice of the present invention, those terms refer to the capability of the structure to have substitution or not on the chemical unit or not. The term 'group' refers to any chemical structure, while the term 'central nucleus' refers specifically to a ring structure as the core chemical moiety. For example, an 'alkyl group' includes unsubstituted n-alkyl, iso-alkyl, methyl ethyl, octyl, iso-octyl, docecyl, and the like, and substituted alkyl such as hydroxymethyl, 1-chloroethyl, 2-cyano-butyl, 3-ethyl-4-hexyl, omega-carboxy-pentyl, and the like. Where the term 'moiety' is used, as in the term alkyl moiety is used, that term refers to only unsubstituted chemical units. Similarly, where the term 'central nucleus' is used, such as in the central nucleus of a naphthyl, any substituent may be present on the central nucleus of the naphthyl group, such as 1-methyl-, 2-chloro-, 2,4-dimethoxy-, 2,2'-dimethoxy-, and the like. Where the term having a structure of the specific formula is used, no substitution is allowed beyond that of the described formula.

Among the substituents that can be considered for the compounds of formula (I) according to the invention, groups should be considered that comprise and/or form at least one function which can be polymerized and/or crosslinked, which group are preferably selected from the following list: alkenyl, advantageously vinyl, methacryloyl, acryloyl, acryloxyalkyl, methacryloxyalkyl or epoxy.

Thus, the photochromic compounds according to the invention can be monomers, of different types or not, that can react with each other or with other comonomers to form homopolymers and/or copolymers that bear a photochromic functionality and possess mechanical properties of macromolecules. It follows that one of the objects of the present invention consists of these homopolymers or copolymers comprising (co)monomers and/or of crosslinked compounds, that, at least in part, consist of photochromic compounds (I) according to the invention.

In the same general concept, the above-mentioned compounds (I) can be crosslinking agents that have one or more reactive functions capable of allowing the formation of bridges between chains of polymers of photochromic nature or not. The crosslinked compounds that can be obtained in this manner also are a part of the present invention.

Amongst such compounds having formula (I) preferred photochromic compounds are those which have the formula (Ia) and (Ib) below:

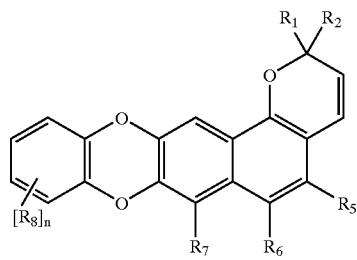

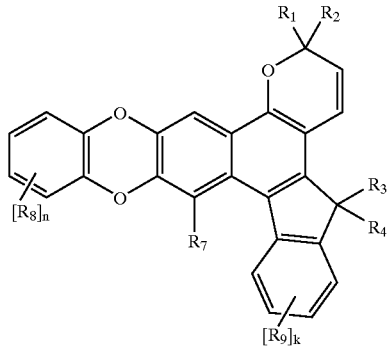

in which:
$R_1$ and/or $R_2$, independently represent optionally substituted aryl or heteroaryl groups the basic structure of which is selected from those of phenyl, naphthyl, biphenyl, pyridyl, furyl, benzofuryl, dibenzofuryl, N—($C_1$–$C_6$)alkylcarbazole, thienyl, benzothienyl, dibenzothienyl, julolidinyl groups; $R_1$ and/or $R_2$ advantageously representing a para-substituted phenyl group, said substituents are selected preferably from alkoxy, dialkylamino, diarylamino, or $R_1$ and $R_2$ together form an adamantyl group or norbornyl group or anthracenylidene group;

$R_3$ and $R_4$ are the same or different, and may represent independently
a hydrogen, a hydroxy, a halogen, a linear, branched, or cyclic alkyl group that comprises 1 to 6 carbon atoms,
a —$OR_{20}$ group, wherein $R_{20}$ is ($C_1$–$C_3$)alkyl, phenyl ($C_1$–$C_3$)alkyl, mono($C_1$–$C_3$)alkylphenyl($C_1$–$C_3$) alkyl, mono($C_1$–$C_3$)alkoxyphenyl($C_1$–$C_3$)alkyl, ($C_1$–$C_3$)alkoxy($C_2$–$C_4$)alkyl, fluoro($C_1$–$C_3$)alkyl, or chloro($C_1$–$C_3$)alkyl,
an optionally substituted phenyl or benzyl group, said substituents being mono, di-, or tri-, and selected from group $R_{20}$,
a —$C(R_{14})_2X$ group, wherein X is hydroxy, alkoxy, benzoyloxy, $C_1$–$C_6$ acyloxy, an ester group: —$COOR_{11}$, an amine or amide group: —$NH_2$, —$NHR_{12}$, —$N(R_{12})_2$, —$CONH_2$, —$CONHR_{12}$, —$CON(R_{12})_2$, $R_{14}$ is hydrogen, $C_1$–$C_6$ alkyl, phenyl or naphthyl with $C_1$–$C_6$ alkyl or $C_1$–$C_6$ alkoxy substituents,
a polyether or polyurea residue,
or $R_3$ and $R_4$ together form a 5- to 7-member optionally substituted spiro-cyclic ring which can comprise at least one heteroatom selected from oxygen, sulfur, and nitrogen, and/or at least one substituent selected from the group consisting of a $C_1$ to $C_6$ alkyl group which is linear or branched, a $C_1$ to $C_6$ alkoxy group which is linear or branched, and an amine group of formula

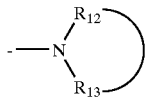

as defined in $R_1$ and $R_2$ of formula (I) for amine groups. The spiro-ring may be annelated with one or two benzene groups $R_5$ and $R_6$ are the same or different, and may represent independently
a hydrogen,
a linear or branched alkyl group that comprises 1 to 6 carbon atoms,
a —$C(R_{14})_2X$ group, wherein X is hydroxy, alkoxy, benzoyloxy, C1–C6 acyloxy, an amine or amide group: —$NH_2$, —$NHR_{12}$, —$N(R_{12})_2$, —$CONH_2$, —$CONHR_{12}$, —$CON(R_{11})_2$, $R_{14}$ is hydrogen, C1–C6 alkyl, phenyl or naphthyl with C1–C6 alkyl or C1–C6 alkoxy substituents,
an optionally substituted phenyl or benzyl group,
a —$COR_{15}$, or —$COOR_{15}$ group, $R_{15}$ representing a linear or branched alkyl group comprising 1 to 6 carbon atoms,
or alternatively, $R_5$ and $R_6$ may together form a 5- to 7-member optionally substituted carbocyclic or heterocyclic ring which can comprise at least one heteroatom selected from oxygen, sulfur, and nitrogen, and/or at least one substituent selected from the group consisting of a C1 to C6 alkyl group which is linear or branched, a C1 to C6 alkoxy group which is linear or branched, and an amine group of formula

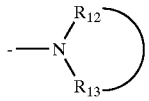

as defined in $R_1$ and $R_2$ for amine groups of formula (I). The ring may be annelated with one aromatic group. Examples of the carbocyclic ring substituents include cyclopentane, cyclohexane, bicylco[2,2,1] heptane, etc. Examples of the heterocyclic group include dihyrofuran, dihydropyran, etc. Examples of the aromatic annelated carbocyclic ring include indeno, dihydronaphthaleno, etc. Examples of the aromatic annelated heterocyclic ring include benzofurano, benzodioxino, etc.;

$R_7$, $R_8$, and $R_9$, which are identical or different, represent, independently
a hydrogen,
a linear or branched alkyl group which comprises 1 to 6 carbon atoms,
a cycloalkyl group comprising 3 to 7 carbon atoms,
a linear or branched alkoxy group comprising 1 to 6 carbon atoms,
a haloalkyl, halocycloalkyl, or haloalkoxy group corresponding to the alkyl, cycloalkyl, alkoxy groups above respectively, which are substituted with at least one halogen atom, notably selected from fluorine, chlorine and bromine,
a linear or branched alkenyl or alkynyl group comprising 1–12 carbon atoms, preferably a vinyl or allyl group,
a linear or branched alkenoxy or alkynoxy group comprising 1–12 carbon atoms, preferably an allyloxy group,
n and k are integer from 0 to 4.

These compounds present particularly advantageous photochromic properties, such as, having strong coloration ability with two distinct, equal intensity absorption bands in the visible range. These compounds are also preferably stable and compatible with matrices made of at least one organic polymer or mineral material (e.g., inert inorganic binder), both in the form included in the matrix and in the form of a coating.

In a solution or in the polymer matrix, the compounds according to the invention are colorless or slightly colored in the initial state and they rapidly develop an intense coloration under UV light (365 nm) or a luminous source of the solar type. They recover to their initial color at an acceptable rate when the irradiation stops.

General Synthetic Procedure for Preparation of the Compounds

The compounds of the invention can be obtained by the condensation of a derivative of 1-naphthol that is suitably substituted and a derivative of propargyl alcohol. The condensation can be carried out in organic solvents, particularly non-polar solvents such as toluene, xylene or tetrahydrofuran and, optionally, in the presence of a catalyst, acid catalysts, and especially acid catalysts such as fluorinated organic acid catalysts, p-toluenesulfonic acid (pTsOH), chloroacetic acid, or acid aluminum oxide:

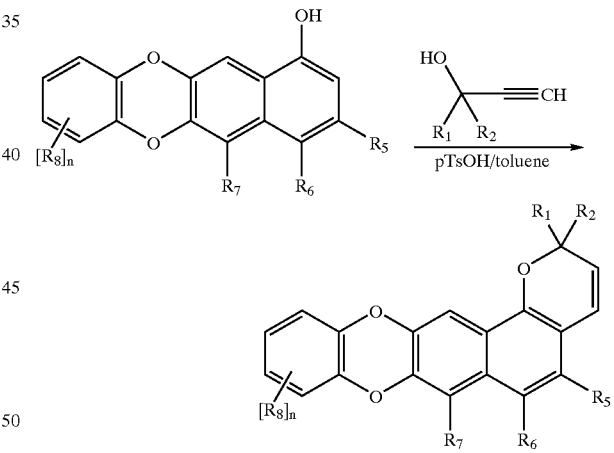

These synthetic routes are classical and have been described in the above-mentioned references of the prior art. The propargyl alcohols are either commercially available or easily synthesized by the reaction of lithium acetylide or ethynyl (magnesium bromide) with the corresponding ketones $R_1C(O)R_2$. The ketones are also either commercially available or easily synthesized by the classical methods, for example, the Friedel-Crafts reaction from an acid chloride.

The derivatives of 1-naphthol are obtained by various methods adapted from the literature. Below we give some references on methods that allow the synthesis of the compounds of the invention.

Scheme 1

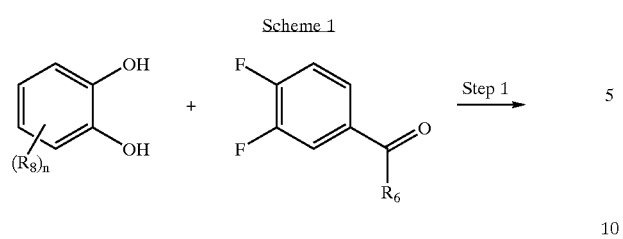

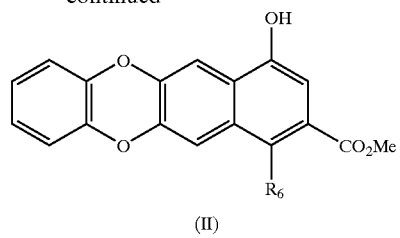

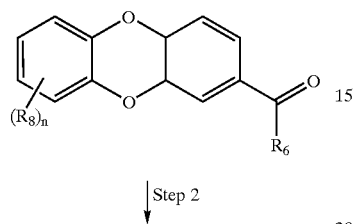

(II)

In Scheme 1, Step 1 is carried out according to a method described by Eastmond and Paprotny (*Chem. Letter*, 1999, No. 6, 479), and Step 2 by Johnson et al. (*Org. Reaction*, 1951, 6, 1). The —COOMe group in (II) can be easily transformed to other groups such as —$CH_2OH$, —$CH_3$, etc. according to the appropriate selection of reagents and groups by one ordinarily skilled in the art.

When the $R_6$ group in Scheme 1 is a substituted phenyl group, more 1-naphthol derivatives can be obtained as illustrated in Schemes 2 and 3:

Scheme 2

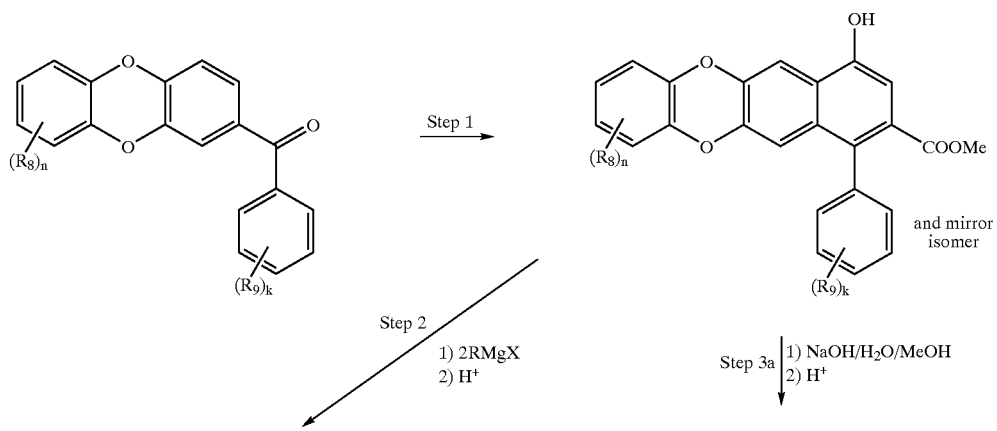

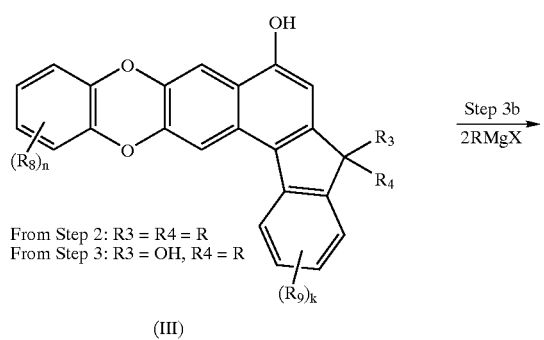

(III)

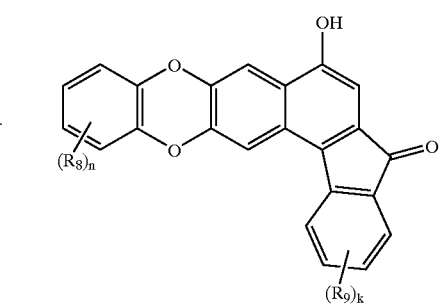

Scheme 3

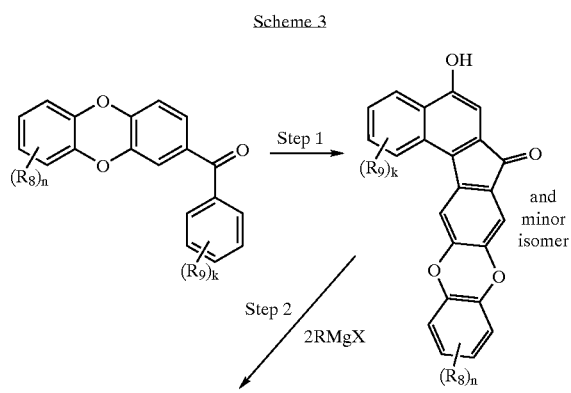

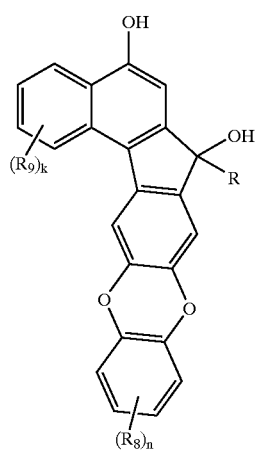

(IV)

In Scheme 2, Step 1 is carried out according to a method described by Johnson et al. (Org. Reaction, 1951, 6, 1). Steps 2 and 3a are classic to ones skilled in the art. The acid used for dehydration can be selected from a group consisting of substituted sulfonic acids, (poly) phosphoric acid, HCl/Acetic acid, etc. FIG. 6b in U.S. Pat. No. 6,225,466 and Reaction F in U.S. Pat. No. 6,296,785 are the best examples for these reactions.

In Scheme 3, Step 1 is carried out according to a method described by FIG. 5 in U.S. Pat. No. 6,225,466, and Step 2 is simply a breakup of carbonyl group by a Grignard reagent.

Scheme 4 gives more 1-naphthol derivatives from Compound IIIa or IVa when the Grignard reagent used in Step 3b of Scheme 2 or Step 2 of Scheme 3 is of the following structure:

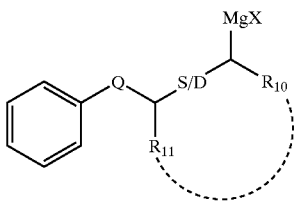

in which Q is selected from the group consisting of oxygen, $CH_2$, and a carbon-carbon bond; $R_{10}$ and $R_{11}$, which are the same or different, independently representing a hydrogen, a linear, branched, or cyclic alkyl group comprising 1 to 6 carbon atoms, an aryl or heteroaryl group, or together representing a ring group that is aromatic or non-aromatic.

Scheme 4

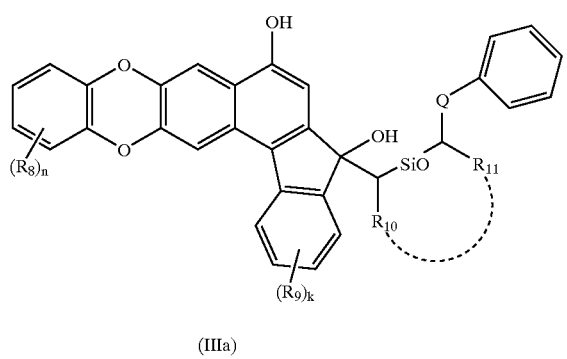

(IIIa)

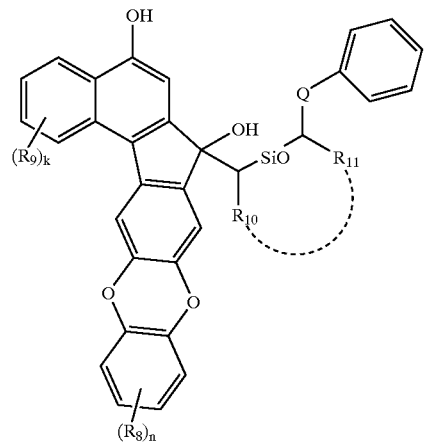

(IVa)

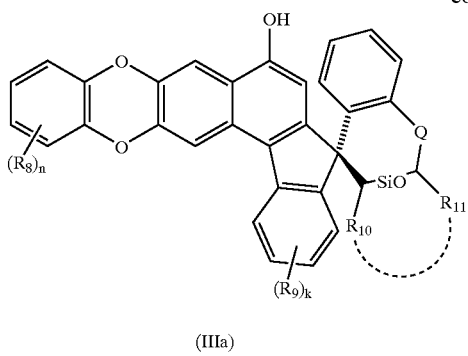

(IIIa)

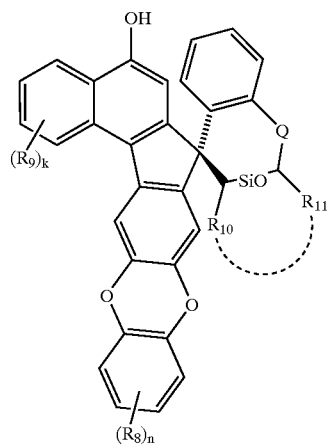

Regarding the commercial application of compounds according to the present invention, it should be noted that the compounds can be used as a photochromic material dispersed in the composition of a polymer matrix. They can also be used in solution.

A photochromic solution can be obtained by dissolving the compound in an organic solvent, such as toluene, dichloromethane, tetrahydrofuran or ethanol. The solutions obtained are generally colorless and transparent. When exposed to sunlight, they develop a strong coloration and they recover the color of this state when placed in an environment with lesser exposure to solar radiation or, in other words, when they are no longer exposed to UV radiation. In general, a very low concentration of products (on the order of 0.01–5% by weight or volume) is sufficient to obtain an intense coloration.

The most interesting applications are those in which the photochrome is dispersed uniformly within or on the surface of a polymer, copolymer or mixture of polymers. The implementation methods that can be considered are of a great variety. Among those known to a person skilled in the art, one can cite, for example, diffusion in the (co)polymer, from a suspension or solution of the photochrome, in a silicone oil, in an aliphatic or aromatic hydrocarbon, in a glycol, or from another polymer matrix. In many cases, the diffusion is carried out at a temperature of 50–200° C. for a duration of 15 minutes to several hours, depending on the nature of the polymer matrix. Another implementation technique consists in mixing the photochrome in a formulation of polymerizable materials, in depositing this mixture on a surface or in a mold and in then carrying out the polymerization. These implementation techniques and others are described in the article by Crano et al. "Spiroxazines and their use in photochromic lenses," published in Applied Photochromic Polymer Systems, Publishers Blackie and Son Ltd., 1992. According to a variant of the invention, it is also possible to consider grafting the photochromes onto (co)polymers. Thus, another aspect of the invention consists of the (co)polymers grafted with at least one of the photochromes described above.

As examples of preferred polymer materials for optical applications of the photochromic compound according to the invention, one can mention the following products: alkyl, cycloalkyl, aryl or arylalkyl poly(mono-, di-, tri-, tetra) acrylate or poly(mono-, di-, tri-, tetra) methacrylate, optionally halogenated or comprising at least ether and/or ester and/or carbonate and/or carbamate and/or thiocarbamate and/or urea and/or amide group; polystyrene, polycarbonate (e.g., bisphenol A polycarbonate, poly(carbonate of diallyl diethylene glycol), polyepoxy, polyurethane, polythiourethane, polysiloxane, polyacrylonitrile, polyamide, aliphatic or aromatic polyester, vinyl polymers, cellulose acetate, cellulose triacetate, cellulose acetate-propionate or polyvinylbutyral, copolymers of two or more types of monomers or mixtures of the above-mentioned polymers, preferably polycarbonate-polyurethane, poly(meth)acrylate-polyurethane, polystyrene-poly(meth)acrylate or polystyrene-polyacrylonitrile, advantageously a mixture of polyester and/or polycarbonate or poly(meth)acrylate.

The quantity of photochrome used in various articles depends on the desired degree of darkening. In particular, it is used in a quantity of 0.001–20 wt % of the total weight of the layer in which the photochrome is included. The photochromic compounds according to the invention can be used alone or in a mixture with other products to form a composition that can be in solid or liquid form, for example, in a solution or in a dispersion, as has already been mentioned above. These compositions, which constitute another object of the invention, can comprise one or more compounds (I) according to the invention and other complementary photochromic compounds which allow the attaining of dark colorations, for example, gray or brown, which the public desires in applications such as ophthalmic or sun-protection eyewear. These additional photochromic compounds can be those known to a person skilled in the art and described in the literature, for example, other naphthopyrans, benzopyrans, chromenes (U.S. Pat. Nos. 3,567,605, 5,238,981, World Patent No. 9,422,850, European Patent No. 562,915), spiropyrans or naphthospiropyrans (U.S. Pat. No. 5,238,981) and spiroxazines (CRANO et al., "Applied Photochromic Polymer Systems," Publishers Blackie & Son Ltd., 1992, Chapter 2).

These compositions according to the invention can also comprise:

Non-photochromic dyes allowing the adjustment of the tint, and/or one or more stabilizers, such as, for example, an antioxidant, and/or one or more anti-UV screens, and/or one or more anti[free]radical agents, and/or deactivators that deactivate the states of photochemical excitation.

These additives can enable further improvements in the durability of said compositions.

According to another one of its aspects pertaining to the application of the photochromic compounds (I), the present invention also relates to ophthalmic articles, such as articles of ophthalmic or sun protection eyewear articles, or eye shields comprising at least one compound according to the invention and/or at least one (co)polymer formed, at least in part, of repeating units derived from compounds having formula (I) and/or at least one composition comprising compounds (I) according to the invention, as defined above, and/or at least one matrix, as defined above, made of an organic polymer material or a mineral material or a mineral-organic hybrid material incorporating at least one compound of the invention.

In practice, the articles to which the present invention applies more particularly are photochromic ophthalmic or sun-protection lenses, glass paneling (glasses for buildings, for locomotion devices, automobiles), optical devices, decorative articles, sun-protection articles, information storage, etc.

The present invention will be better understood in the light of the following examples of synthesis and photochromic validation of compounds having the general formula (I). These examples are not intended to be interpreted as limiting the invention, but rather, show specific aspects of the invention within the broad generic scope disclosed.

EXAMPLES

Example 1

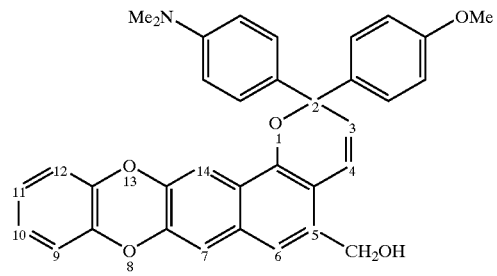

Step 1: Oxanthrene-2-carbaldehyde was obtained by reacting pyrocatechol and 3,4-difluorobenzaldehye according to the protocol described in *Chem. Letter*, 1999, No. 6, 479.

Step 2: Oxanthrene-2-carbaldehyde from Step 1 (6 g), dimethyl succinate (5.4 g), and potassium t-butoxide (4.3 g) were mixed in 110 ml of toluene. The mixture was refluxed for 2 hours under nitrogen blanket. After it was cooled to room temperature, 100 ml of water was added and mixed well. The aqueous phase was separated, acidified with 5N HCl, and extracted with 3×100 ml of ethyl acetate. The combined extracts were washed once with water, dried over magnesium sulfate. The solvent was removed under reduced pressure to give 15 g of honey-like crude half-ester product. It was known that the crude product contained some aliphatic oil contaminants from the ethyl acetate solvent. It was used without purification.

Step 3: The crude half-ester from Step 2 (15 g) was added to reaction flask containing 46 ml of acetic anhydride and 6 g of anhydrous potassium acetate. The mixture was refluxed for 4 hours, cooled, filtered. The solid in the filtration funnel was washed thoroughly with ethyl acetate. The combined filtrate was concentrated to just dry under vacuum. The dark solid was re-dissolved in ethyl acetate and washed with water, dried over magnesium sulfate. The organic solution was concentrated under reduced pressure. The residual was subjected to a flash silica column with ethyl acetate/hexane 1:4 as elutant. The desired product was obtained in the oil carried over from Step 2. It was used without further separation.

Step 4: The oil from Step 3 (5 grams) was added to a reaction flask containing 75 mL of methanol. After adding 0.5 ml of concentrated HCl, the mixture was refluxed for 5 hours. The reaction solution was concentrated, then subjected to a silica column with ethyl acetate/hexane 1:4 as elutant yielding 0.2 g of yellow powder. An NMR spectrum showed the product to have a structure consistent with 10-hydroxy-benzo[b]-naphtho[2,3-e]-[1,4]dioxine-8-carboxylic acid methyl ester.

Step 5: The product from Step 4 (0.20 grams) was added to a reaction flask containing 1-(4-methoxyphenyl)-1-(4-N,N-dimethylaminophenyl)-2-propyn-1-ol (0.25 grams), 20 mL of toluene. After the mixture started to reflux, catalytic amount of p-toluenesulfonic acid was added. The reaction mixture was refluxed overnight, cooled, concentrated with a rotary evaporator. Purification of the residue by a silica column chromatography with ethyl acetate/hexane 1:4 as elutant offered 0.14 grams of light yellow solid product. An NMR spectrum showed the product to have a structure consistent with 2-(4-methoxyphenyl)-2-(4-N,N-dimethylaminophenyl)-5-methoxycarbonyl-2H-(benzo[b]dioxino[2,3-b]naphtho)[1,2-b]pyran.

Step 6: The product from Step 5 (140 milligrams) was dissolved in anhydrous tetrahydrofuran (10 mL) in a reaction flask. The solution was cooled in an ice bath and covered with nitrogen blanket while 1.1 equivalent of DIBAL-H (1M solution in toluene) was added with stirring. After stirring an additional 15 minutes with the ice bath removed, the reaction was quenched with few drop of water, then dried over magnesium sulfate, and filtered. The filtrate was concentrated by rotary evaporation. The residue was chromatographed on silica gel using a 4:1 v/v mixture of hexane and ethyl acetate as the elutant. The photochromic fractions were collected, dried by rotary evaporation yielding 100 milligrams of the desired product. An NMR spectrum showed the product to have a structure consistent with 2-(4-methoxyphenyl)-2-(4-N,N-dimethylaminophenyl)-5-hydroxymethyl-2H-(benzo[b]dioxino[2,3-b]naphtho)[1,2-b]pyran.

Example 2

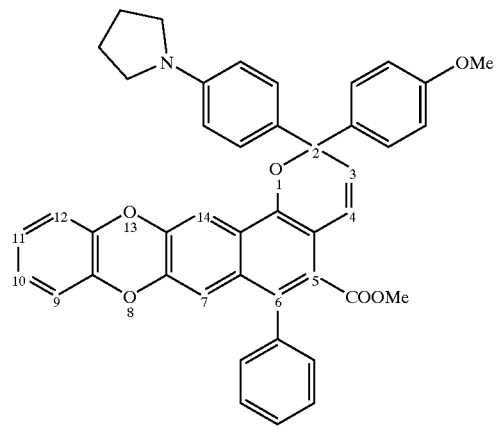

2-(4-methoxyphenyl)-2-(4-pyrrolidinophenyl)-5-methoxycarbonyl-6-phenyl-2H-(benzo[b]dioxino[2,3-b]naphtho)[1,2-b]pyran was obtained by following the process of Example 1, replacing oxanthrene-2-carbaldehyde with 2-benzoyl oxanthrene in Step 2. The structure was confirmed by a NMR spectrum.

Example 3

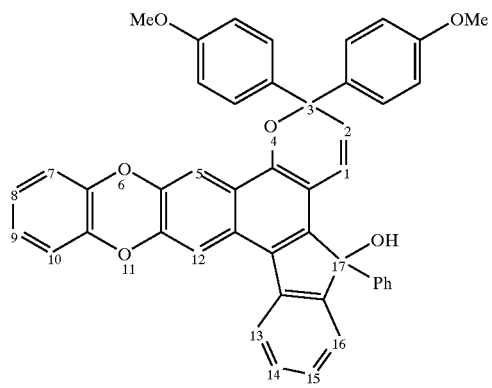

Step 1 to 3: 10-acetyloxy-benzo[b]-naphtho[2,3-e]-[1,4] dioxine-8-carboxylic acid methyl ester was obtained by following the corresponding steps in Example 1, and replacing oxanthrene-2-carbaldehyde with 2-benzoyl oxanthrene in Step 2.

Step 4: The light yellow solid product (10-acetyloxy-benzo[b]-naphtho[2,3-e]-[1,4]dioxine-8-carboxylic acid methyl ester) from Step 3 (1.20 grams) was added to a reaction flask containing 50 mL of water, 6 ml of 5N sodium hydroxide, and 10 mL of methanol. The mixture was refluxed overnight and cooled to give a clear brown solution. It acidified with 5N hydrochloric acid. The precipitate was collected with filtration, and washed with water for 3 times. A beige powder (0.83 g) was obtained after drying the precipitate in a vacuum oven. An NMR spectrum showed the product to have a structure consistent with 10-hydroxy-benzo[b]-naphtho[2,3-e]-[1,4]dioxine-8-carboxylic acid.

Step 5: The product from Step 4 (2.0 grams), 10 mL of toluene and 2.0 grams of p-toluenesulfonic acid were added to a reaction flask fitted with a Dean-Stark trap. The resulting mixture was heated to reflux for 6 and one half hours. A deep red solid precipitate formed. The mixture was cooled and 40 ml of water was added. The solid was collected by vacuum filtration, re-dissolved in 100 ml of ethyl acetate, washed with 5% sodium carbonate solution, and thoroughly washed with water. The organic phase was dried over magnesium sulfate, filtered, and the filtrate was dried with rotary evaporation to yield 0.5 grams of a red-brown solid product. An NMR spectrum showed the product to have a structure consistent with 11-oxo-benzo[b]-indeno[3,2-a]naphtho[2,3-e]-[1,4]dioxin-13-ol.

Step 6: The product from Step 5 (0.20 grams) was added to a reaction flask containing 1,1-di(4-methoxyphenyl)-1-phenyl-2-propyn-1-ol (0.25 grams), 15 mL of toluene. After the mixture started to reflux, catalytic amount of p-toluenesulfonic acid was added. The reaction mixture was refluxed for 1 hour, cooled, concentrated. The residue was chromatographed on silica gel using 4:1 v/v mixture of hexane and ethyl acetate as the elutant to offer 0.15 grams of desired product in red-brown solid. The structure was confirmed by an NMR spectrum to be 3,3-di(4-methoxyphenyl)-17-oxo-3H-(benzo[b]dioxino[2,3-b]-indeno[3,2-a]-naphtho)[1,2-b]pyran.

Step 7: The product from Step 6 (100 milligrams) was dissolved in anhydrous tetrahydrofuran (15 mL) in a reaction flask under nitrogen blanket. Excess amount of phenyl magnesium bromide (3M solution in ether) was added dropwise while cooling with an ice/water bath. The reaction solution was then stirred at room temperature for 30 minutes. The reaction mixture was diluted with 10 ml toluene and quenched with 10 ml saturated ammonium chloride solution. The layers were separated and the organic layer was concentrated by rotary evaporation. The residue was chromatographed on silica gel using a 4:1 v/v mixture of hexane and ethyl acetate as the elutant. The photochromic fractions were collected, dried by rotary evaporation yielding 25 milligrams of the desired product. An NMR spectrum showed the product to have a structure consistent with 3,3-di(4-methoxyphenyl)-17-hydroxy-17-phenyl-3H-(benzo[b]dioxino[2,3-b]-indeno[3,2-a]-naphtho)[1,2-b]pyran.

Photochromic Property Measurement

Each of the invention compounds is dissolved in chloroform at a concentration of 0.1%. The UV-visible absorptions (optical path of 1 cm) are then measured before and after exposure to a 365 nm UV source for 1 minutes. The photochromic properties: $\lambda_{UV}$ (absorption wavelength closet to visible spectrum before activated), $\lambda_{max}$ of the two principle absorption bands ($\lambda_{Vis,1}$ and $\lambda_{Vis,2}$), and bleaching rate ($t_{1/2}$ in seconds) of these compounds are listed in the following table.

TABLE 1

| Example compound | $\lambda_{UV}$ (nm) | $\lambda_{Vis,1}$ (nm) | $\lambda_{Vis,2}$ (nm) | Bleach ($t_{1/2}$, sec.) |
|---|---|---|---|---|
| 1 | 360 | 500 (shoulder) | 568 | 14 |
| 2 | 380 | 505 | 610 | 6 |
| 3 | 400 | 445 | 580 | 19 |

It is thus demonstrated by these measurements that the naphthopyrans of the invention have two distinct absorption peaks, their bands cover majority of the visible spectrum. They display high intensity when activated by solar radiation. Relative intensity between the two bands stays close to unity regardless the substituent groups and solvents. In addition, it has been observed that they exhibit high sensitivity to solar radiation due to high UV $\lambda_{max}$.

Although the present invention has been described with reference to the specific details of particular embodiments thereof, it is not intended that such details be regarded as limitations upon the scope of the invention except as and to the extent that they are included in the accompanying claims.

What is claimed is:

1. A photochromic naphthopyran having a central nucleus of the

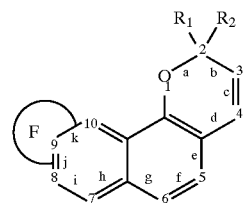

formula:

wherein F is a 1,4-benzodioxine ring having the following graphic formulae:

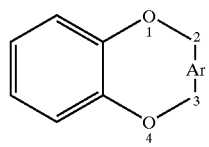

with its 2,3 positions fused to the i, j, or k side;

$R_1$ and $R_2$ are atoms or groups providing photochromic properties to the naphthopyran.

2. The photochromic naphthopyran of claim 1, characterized in that it has the following structure:

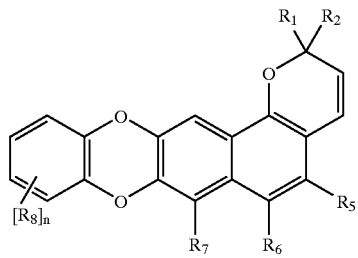

wherein, $R_1$ and/or $R_2$, independently represent optionally substituted aryl or heteroaryl groups the basic structure of which is selected from those of phenyl, naphthyl, biphenyl, pyridyl, furyl, benzofuryl, dibenzofuryl, N—($C_1$-$C_6$)alkylcarbazole, thienyl, benzothienyl, dibenzothienyl, julolidinyl groups; $R_1$ and/or $R_2$ representing a para-substituted phenyl group, said substituents of the phenyl group are selected from the group consisting of alkoxy, dialkylamino, diarylamino, or $R_1$ and $R_2$ together form an adamantyl group or norbornyl group or anthracenylidene group; either $R_1$ or $R_2$ is mono- or di-substituted phenyl which is substituted in the position para to the connection side with -phenyl, —(CH2)$_p$-phenyl or —O—(CH2)$_p$-phenyl substituted, wherein p is an integer from 1 to 6, and the ring of the substituent group forms part of a second photochromic pyran;

$R_5$ and $R_6$ are the same or different, and may represent independently
a hydrogen,
a linear or branched alkyl group that comprises 1 to 6 carbon atoms,
a —C($R_{14}$)$_2$X group, wherein X is hydroxy, alkoxy, benzoyloxy, $C_1$-$C_6$ acyloxy, an amine or amide group: —NH$_2$, —NHR$_{12}$, —N(R$_{12}$)$_2$, —CONH$_2$, —CONHR$_{12}$, —CON(R$_{11}$)$_2$, $R_{14}$ is hydrogen, $C_1$-$C_6$ alkyl, phenyl or naphthyl with $C_1$-$C_6$ alkyl or $C_1$-$C_6$ alkoxy substituents,
an optionally substituted phenyl or benzyl group,
a —COR$_{15}$, or —COOR$_{15}$ group, $R_{15}$ representing a linear or branched alkyl group comprising 1 to 6 carbon atoms,
or alternatively, $R_5$ and $R_6$ may together form a 5- to 7-member optionally substituted carbocyclic or heterocyclic ring comprising a heteroatom selected from oxygen, sulfur, and nitrogen and wherein said substituents are selected from the group consisting of a C1 to C6 alkyl group which is linear or branched, a C1 to C6 alkoxy group which is linear or branched, and an amine group of formula

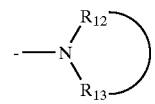

wherein $R_{12}$ and $R_{13}$, which are the same or different, independently represent a hydrogen, a linear, branched, or cyclic alkyl group comprising 1 to 6 carbon atoms, an aryl or heteroaryl group consisting of C atoms and a heteroatom selected from the group consisting of N, S or O ring atoms, or representing, together with the nitrogen atom to which they are bound, a 5- to 7-membered ring selected from the group consisting of pyridyl, furyl, benzofuryl, dibenzofuryl, thienyl, and benzothienyl, said nitrogen atom in the 5- to 7-membered ring being optionally substituted with an $R_{10}$ group, which $R_{10}$ is a linear or branched alkyl group comprising 1 to 6 carbon atoms, a phenyl, a benzyl, or a naphthyl group.

$R_7$, and $R_8$ are independently
a hydrogen,
a linear or branched alkyl group which comprises 1 to 6 carbon atoms,
a cycloalkyl group comprising 3 to 7 carbon atoms,
a linear or branched alkoxy group comprising 1 to 6 carbon atoms,
a haloalkyl, halocycloalkyl, or haloalkoxy group where alkyl groups comprise $C_1$-$C_6$ alkyl groups, $C_1$-$C_6$ haloalkoxy groups above respectively, which are substituted with at least one halogen atom, selected from fluorine, chlorine and bromine,
a linear or branched alkenyl or alkynyl group comprising 1–12 carbon atoms, a linear or branched alkenoxy or alkynoxy group comprising 1–12 carbon atoms, and n is an integer from 0 to 4.

3. A photochromic naphthopyran having a central nucleus of the formula

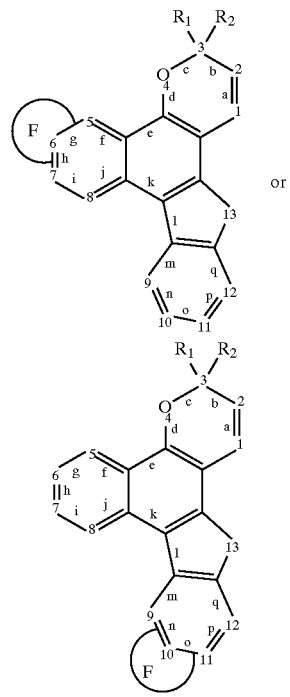

wherein F is a 1,4-benzodioxine ring having the following graphic formulae:

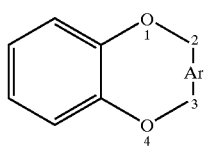

with its 2,3 positions fused to the i, j, or k side;

$R_1$ and $R_2$ are atoms or groups providing photochromic properties to the naphthopyran, and F, with its 2,3 positions, is fused to the g, h, i, n, o, or p side.

4. The photochromic naphthopyran of claim 3, characterized in that it has the following structure wherein, $R_7$, and $R_8$ are independently
- a hydrogen,
- a linear or branched alkyl group which comprises 1 to 6 carbon atoms,
- a cycloalkyl group comprising 3 to 7 carbon atoms,
- a linear or branched alkoxy group comprising 1 to 6 carbon atoms,
- a haloalkyl, halocycloalkyl, or haloalkoxy group where alkyl groups comprise $C_1$–$C_6$ alkyl groups, $C_1$–$C_6$ haloalkoxy groups above respectively, which are substituted with at least one halogen atom, notably selected from fluorine, chlorine and bromine,
- a linear or branched alkenyl or alkynyl group comprising 1–12 carbon atoms, a linear or branched alkenoxy or alkynoxy group comprising 1–12 carbon atoms, and
- n is an integer from 0 to 4, $R_9$ independently represents groups as defined for $R_8$;

k is an integer from 0 to 2;

$R_3$ and $R_4$ are the same or different, and may represent independently
- a hydrogen, a hydroxy, a halogen,
- a linear, branched, or cyclic alkyl group that comprises 1 to 6 carbon atoms,
- a —$OR_{20}$ group, wherein $R_{20}$ is (C1–C3)alkyl, phenyl (C1–C3)alkyl, mono(C1–C3)alkylphenyl(C1–C3) alkyl, mono(C1–C3)alkoxyphenyl(C1–C3)alkyl, (C1–C3)alkoxy, (C2–C4)alkyl, fluoro(C1–C3)alkyl, chloro(C1–C3)alkyl, or optionally substituted phenyl groups,
- an optionally substituted aryl group, said substituents being mono, di-, or tri-, and selected from group $R_{20}$, and $OR_{20}$,
- a —$C(R_{14})_2X$ group, wherein X is hydroxy, alkoxy, benzoyloxy, C1–C6 acyloxy, an ester group: —$COOR_{11}$, an amine or amide group: —$NH_2$, —$NHR_{12}$, —$N(R_{12})_2$, —$CONH_2$, —$CONHR_{12}$, —$CON(R_{12})_2$, $R_{14}$ is hydrogen, C1–C6 alkyl, phenyl or naphthyl with C1–C6 alkyl or C1–C6 alkoxy substituents,
- a polyether or polyurea residue,
- or $R_3$ and $R_4$ together form a 5- to 7-member optionally substituted spiro-cyclic ring comprising a heteroatom selected from oxygen, sulfur, and nitrogen, and which spirocyclic ring may be annelated with one or two benzene groups, the substituents on said 5- to 7-member ring being selected from the group consisting of a C1 to C6 alkyl group which is linear or branched, a C1 to C6 alkoxy group which is linear or branched, and an amine group of formula $$-N\begin{pmatrix} R_{12} \\ R_{13} \end{pmatrix}$$

wherein $R_{12}$ and $R_{13}$ are selected from the group consisting of hydrogen, a linear, branched, or cyclic alkyl group comprising 1 to 6 carbon atoms, an aryl or heteroaryl group consisting of C atoms and a N, S or O ring atom, or representing, together with the nitrogen atom to which they are bound, a 5- to 7-membered ring selected from the group consisting of pyridyl, furyl, benzofuryl, dibenzofuryl, thienyl, and benzothienyl.

5. A photochromic article comprising a light permeable matrix having applied thereto or dispersed or diffused therein a photochromic amount of a photochromic naphthopyran according to claim 1.

6. A photochromic article comprising a light permeable matrix having applied thereto or dispersed or diffused therein a photochromic amount of a photochromic naphthopyran according to claim 2.

7. A photochromic article comprising a light permeable matrix having applied thereto or dispersed or diffused therein a photochromic amount of a photochromic naphthopyran according to claim 3.

8. A photochromic article comprising a light permeable matrix having applied thereto or dispersed or diffused therein a photochromic amount of a photochromic naphthopyran according to claim 4.

9. The photochromic naphthopyran of claim 1 wherein $R_1$ and $R_2$ are selected from the group consisting of hydrogen atoms, halogen atoms, and organic groups.

10. The photochromic naphthopyran of claim 1 wherein $R_1$ and $R_2$ are selected from the group consisting of hydrogen atoms and organic groups.

11. The photochromic naphthopyran of claim 1 wherein $R_1$ and $R_2$ are selected from the group consisting of hydrogen atoms, aliphatic groups, aryl groups, and heterocyclic groups.

12. The photochromic naphthopyran of claim 1 wherein $R_1$ and $R_2$ are selected from the group consisting of a) hydrogen atoms, b) a linear or branched alkyl group of 1 to 12 carbon atoms, c) a cycloalkyl group of 3 to 12 carbon atoms, d) an aryl group of 6 to 24 ring carbon atoms, e) a heteroaryl group of 4 to 24 carbon atoms and at least one hetero ring atom selected from sulfur, oxygen and nitrogen; and f) wherein $R_1$ and $R_2$ together form a heterocyclic ring.

13. The photochromic naphthopyran of claim 9 wherein the heterocyclic ring formed from $R_1$ and $R_2$ is selected from the group consisting of an adamantyl, norbornyl, fluorenylidene, di($C_1$–$C_6$)alkylanthracenylidene and spiro ($C_5$–$C_6$)cycloalkylanthracenylidene group.

14. A photochromic article comprising a light permeable matrix having applied thereto or dispersed or diffused therein a photochromic amount of a photochromic naphthopyran according to claim 9.

15. A photochromic article comprising a light permeable matrix having applied thereto or dispersed or diffused therein a photochromic amount of a photochromic naphthopyran according to claim 10.

16. A photochromic article comprising a light permeable matrix having applied thereto or dispersed or diffused therein a photochromic amount of a photochromic naphthopyran according to claim 11.

17. A photochromic article comprising a light permeable matrix having applied thereto or dispersed or diffused therein a photochromic amount of a photochromic naphthopyran according to claim 12.

18. A photochromic article comprising a light permeable matrix having applied thereto or dispersed or diffused therein a photochromic amount of a photochromic naphthopyran according to claim 13.

19. A photochromic naphthopyran having a central nucleus of the formula:

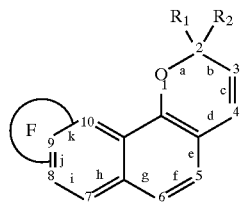

wherein F is a 1,4-benzodioxine ring having the following graphic formulae:

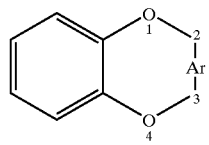

with its 2,3 positions fused to the i, j, or k side;

$R_1$ and $R_2$ are selected from the group consisting of phenyl and substituted phenyl.

20. A photochromic naphthopyran having a central nucleus of the formula

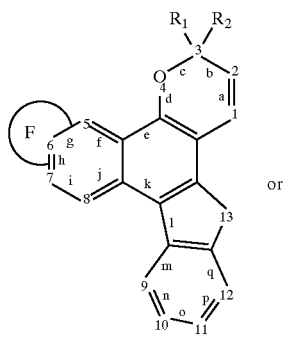

or

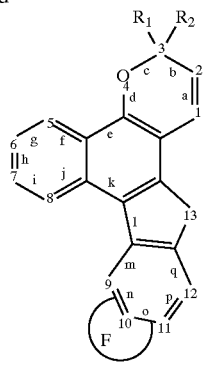

wherein F is a 1,4-benzodioxine ring having the following graphic formulae:

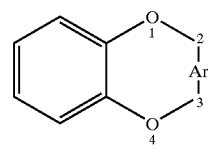

with its 2,3 positions fused to the i, j, or k side; and $R_1$ and $R_2$ are phenyl groups providing photochromic properties to the naphthopyran, and F, with its 2,3 positions, is fused to the g, h, i, n, o, or p side.

21. The photochromic naphthopyran of claim 20, characterized in that it has the following structure

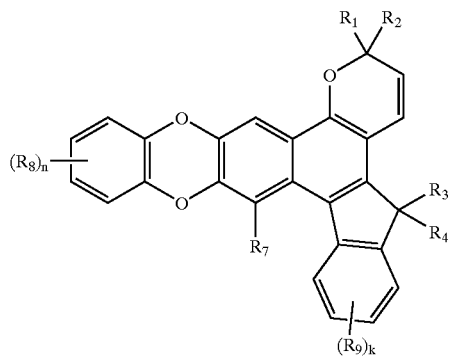

wherein,
$R_7$, and $R_8$ are independently
  a hydrogen,
  a linear or branched alkyl group which comprises 1 to 6 carbon atoms,
  a cycloalkyl group comprising 3 to 7 carbon atoms,
  a linear or branched alkoxy group comprising 1 to 6 carbon atoms,
  a haloalkyl, halocycloalkyl, or haloalkoxy group where alkyl groups comprise $C_1$–$C_6$ alkyl groups, $C_1$–$C_6$ haloalkoxy groups above respectively, which are substituted with at least one halogen atom selected from fluorine, chlorine and bromine,
  a linear or branched alkenyl or alkynyl group comprising 1–12 carbon atoms, a linear or branched alkenoxy or alkynoxy group comprising 1–12 carbon atoms, and n is an integer from 0 to 4,
$R_9$ independently represents groups as defined for $R_8$;
k is an integer from 0 to 2;

$R_3$ and $R_4$ are the same or different, and may represent independently a hydrogen, a hydroxy, a halogen, a linear, branched, or cyclic alkyl group that comprises 1 to 6 carbon atoms, a —$OR_{20}$ group, wherein $R_{20}$ is (C1–C3)alkyl, phenyl(C1–C3)alkyl, mono(C1–C3)alkylphenyl(C1–C3)alkyl, mono(C1–C3)alkoxyphenyl(C1–C3)alkyl, (C1–C3)alkoxy, (C2–C4)alkyl, fluoro(C1–C3)alkyl, chloro(C1–C3)alkyl, or optionally substituted phenyl groups, an optionally substituted aryl group, said substituents being mono, di-, or tri-, and selected from group $R_{20}$, and $OR_{20}$, a —$C(R_{14})_2X$ group, wherein X is hydroxy, alkoxy, benzoyloxy, C1–C6 acyloxy, an ester group: —$COOR_{11}$, an amine or amide group: —$NH_2$, —$NHR_{12}$, —$N(R_{12})_2$, —$CONH_2$, —$CONHR_{12}$, —$CON(R_{12})_2$, $R_{14}$ is hydrogen, C1–C6 alkyl, phenyl or naphthyl with C1–C6 alkyl or C1–C6 alkoxy substituents, a polyether or polyurea residue, or $R_3$ and $R_4$ together form a 5- to 7-member optionally substituted spiro-cyclic ring which comprising one heteroatom selected from oxygen, sulfur, and nitrogen, and which spirocyclic ring may be annelated with one or two benzene groups, the substituents on said 5- to 7-member ring being selected from the group consisting of a C1 to C6 alkyl group which is linear or branched, a C1 to C6 alkoxy group which is linear or branched, and an amine group of formula

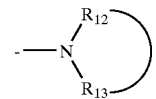

wherein $R_{12}$ and $R_{13}$ are selected from the group consisting of hydrogen, a linear, branched, or cyclic alkyl group comprising 1 to 6 carbon atoms, an aryl or heteroaryl group consisting of C atoms and one N, S or O ring atoms, or representing, together with the nitrogen atom to which they are bound, a 5- to 7-membered ring selected from the group consisting of pyridyl, furyl, benzofuryl, dibenzofuryl, thienyl, and benzothienyl.

* * * * *